(12) United States Patent  
Kribbe

(10) Patent No.: US 8,486,126 B2
(45) Date of Patent: Jul. 16, 2013

(54) LIGHTING SYSTEM FOR USE IN LIGHT THERAPY

(76) Inventor: Ed Kribbe, Norwich (GB)

(*) Notice: Subject to any disclaimer, the term of this patent is extended or adjusted under 35 U.S.C. 154(b) by 549 days.

(21) Appl. No.: 12/763,359

(22) Filed: Apr. 20, 2010

(65) Prior Publication Data

US 2011/0106224 A1 May 5, 2011

(30) Foreign Application Priority Data

Apr. 20, 2009 (EP) .................... 09158256

(51) Int. Cl.
*A61N 5/06* (2006.01)
*A61B 18/18* (2006.01)

(52) U.S. Cl.
USPC .............. 607/91; 607/88; 607/89; 607/90; 607/92; 607/93; 607/94; 606/2

(58) Field of Classification Search
USPC ............................. 607/88–94; 606/2
See application file for complete search history.

(56) References Cited

U.S. PATENT DOCUMENTS

| 5,814,078 | A | 9/1998 | Zhou et al. | |
| 6,623,511 | B1* | 9/2003 | Daffer et al. | 607/82 |
| 7,131,989 | B2* | 11/2006 | Anderer | 607/88 |
| 7,131,990 | B2* | 11/2006 | Bansal et al. | 607/90 |
| 2002/0120312 | A1 | 8/2002 | Ignatius et al. | |
| 2004/0181268 | A1 | 9/2004 | Anderer | |
| 2005/0004631 | A1* | 1/2005 | Benedict | 607/88 |
| 2005/0075703 | A1* | 4/2005 | Larsen | 607/88 |
| 2006/0030907 | A1* | 2/2006 | McNew | 607/88 |
| 2006/0199715 | A1* | 9/2006 | Leon | 482/148 |
| 2007/0021806 | A1* | 1/2007 | Mercier et al. | 607/88 |
| 2007/0073283 | A1 | 3/2007 | Gomes | |
| 2007/0203432 | A1* | 8/2007 | McNew | 601/15 |
| 2008/0285227 | A1 | 11/2008 | Kennard et al. | |
| 2009/0012588 | A1* | 1/2009 | Springer, Jr. | 607/94 |
| 2009/0326424 | A1* | 12/2009 | Shrestha | 601/47 |
| 2010/0076529 | A1* | 3/2010 | Tucker et al. | 607/90 |
| 2011/0098777 | A1* | 4/2011 | Silverstone | 607/45 |
| 2011/0202116 | A1* | 8/2011 | Barolet et al. | 607/90 |
| 2013/0066404 | A1* | 3/2013 | Tapper et al. | 607/90 |

FOREIGN PATENT DOCUMENTS

| WO | 2006/028461 A2 | 3/2006 |
| WO | 2006/059889 A1 | 6/2006 |
| WO | 2007/091188 A2 | 8/2007 |

OTHER PUBLICATIONS

Extended European Search Report, dated Jul. 29, 2009, from corresponding European application.

* cited by examiner

*Primary Examiner* — Jessica Stultz
*Assistant Examiner* — Delma R Forde
(74) *Attorney, Agent, or Firm* — Young & Thompson

(57) ABSTRACT

A method and device for light color therapy, which is a method for simultaneously exposing specific surface regions of the human body to light of specific but possibly different frequencies, temporal characteristics and polarization. The device is constructed to match anatomical details of the human body such as to apply the simultaneous local light exposures to the desired body regions and to compensate for possible movement of the head, thereby minimizing the time required for a single treatment.

12 Claims, 4 Drawing Sheets

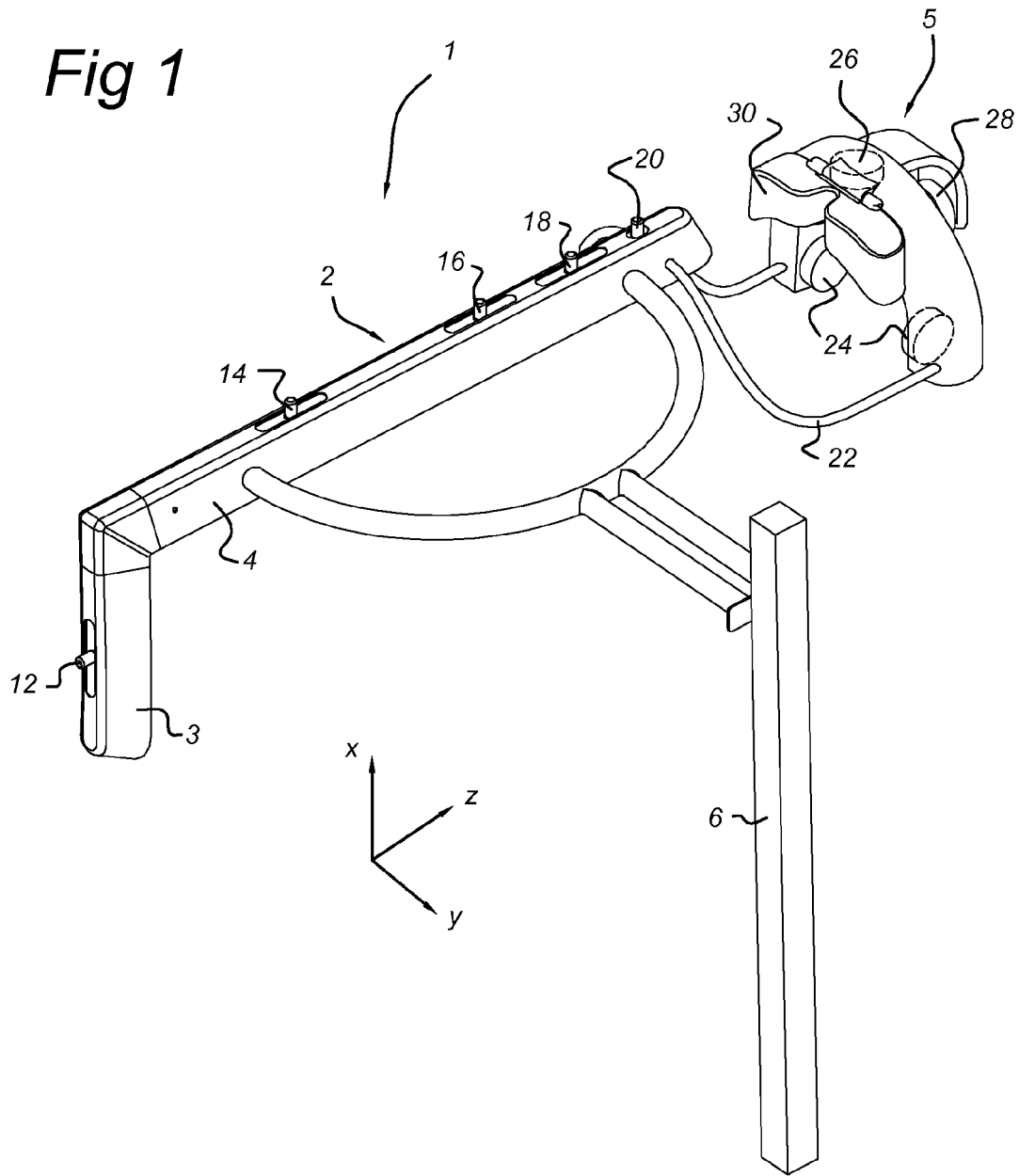

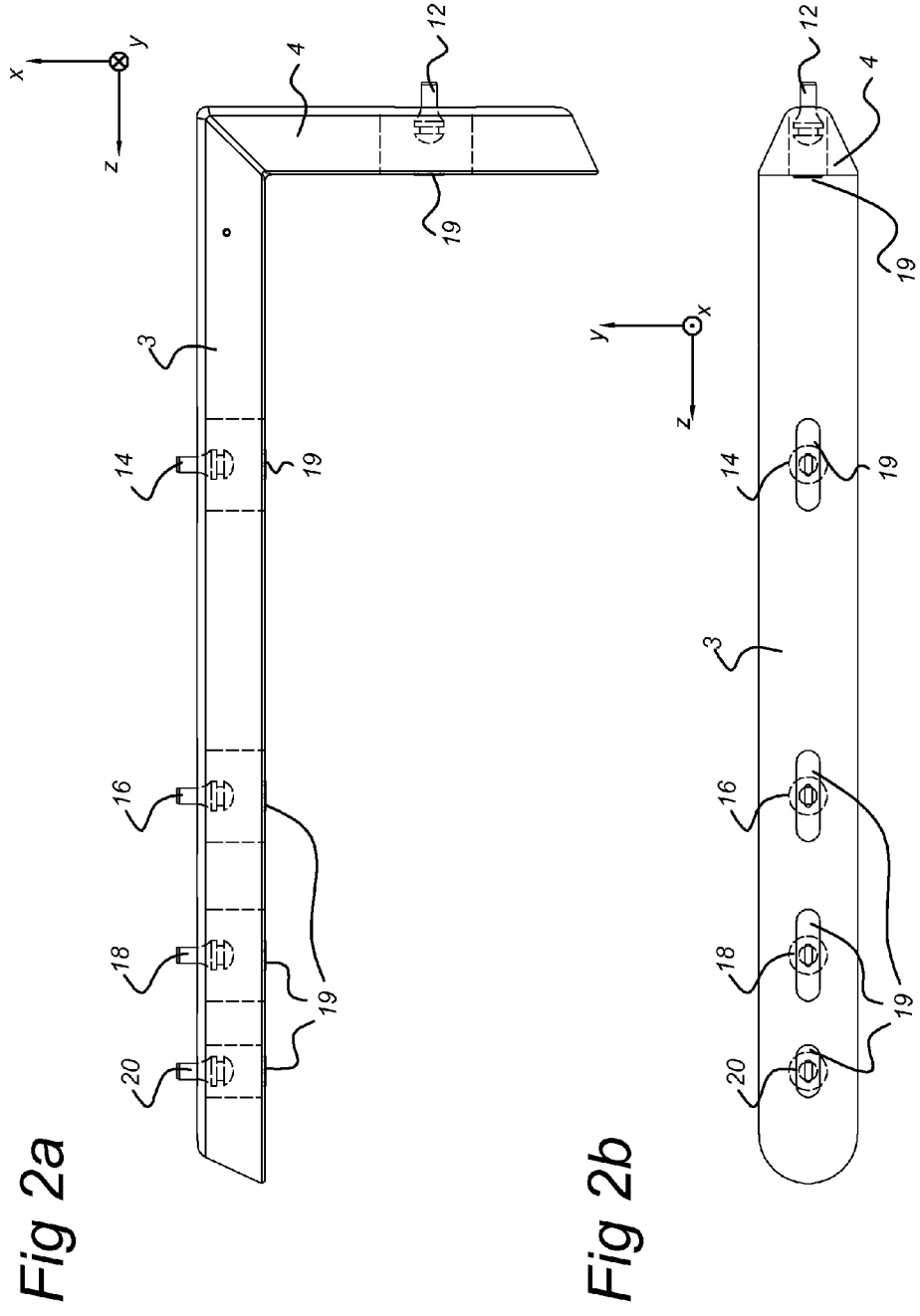

LIGHTING SYSTEM FOR USE IN LIGHT THERAPY

FIELD

The present invention relates to a lighting system for use in light therapy and a method of performing light therapy on a subject.

BACKGROUND

Light therapy (phototherapy) is a form of treatment in which a subject is exposed to light sources of specific frequencies. The light sources can vary according to the desired therapeutic effects and are selected based on their temporal, energetic, angular momentum and other characteristics.

It has been found that stimulation of the skin, possibly with non-coherent sources of light, yields beneficial results. An advantage of light therapy is the absence of any side effects, certainly if ordinary visible light with intensity comparable to day light is used.

Currently available devices tend to limit the exposure of light to easily accessible localized areas of an individual's body, using a single light source with adjustable characteristics. U.S. Pat. No. 7,131,989 discloses a light therapy system that exposes multiple regions of a patient's body to light with specific frequencies in an effort to assist the body in rejuvenating itself. The light therapy system enables simultaneous exposure from light sources arranged in an arbitrary planar configuration, preferably in a single line conforming to the major axis of the human body.

As a representative light therapy treatment last for several minutes or more, it is particularly difficult to keep the head motionless all throughout the therapy session. Currently available multiple lamp devices have sources that remain stationary during a treatment session and therefore will not compensate for head movement, resulting in reduced illumination efficiency.

It would be beneficial to provide a system and a method for improving the efficiency of light therapy treatment by means of improving the ability to concentrate the exposure of light to local areas and reducing the time required for treatment.

SUMMARY

It is an object to provide a lighting system for light color therapy, which enables simultaneous exposure of the various body regions to light of possibly different frequencies, polarizations and temporal characteristics and which overcomes or reduces the disadvantages of the prior art.

According to an aspect, this object is achieved by a lighting system comprising a beam fitting, a head set separated with respect to the beam fitting, and a control unit. The beam fitting extends in a longitudinal direction and comprises a first set of light sources. The head set comprises a second set of light sources. Each light source of the first set and second set of light sources is connected to the control unit, and the control unit is arranged for controlling the emission characteristics of each of the light sources. The light sources of the first set are arranged along the longitudinal direction of the beam fitting at first pre-determined locations. Furthermore, the beam fitting is arranged to be positioned over a trunk and loin of a human being, substantially parallel to a long central body axis. At least one light source of the first set is provided in a recess in the beam fitting, with the recess being arranged for adjusting the first pre-determined location of the at least one light source along the longitudinal direction. At least one light source of the first set is arranged for illuminating trunk and loin portions of the human being, when the beam fitting is positioned over the trunk and loin. In addition, the head set is arranged to be positioned on a head of the human being. The light sources of the second set are arranged at second pre-determined locations on the head set and arranged to direct their light energy at the forehead, the temples and the crown of the human being.

Advantageously, such a lighting system is designed to match anatomical details of the human body such as to apply the simultaneous local light exposures to the desired body regions and to compensate for possible movement of the head. Furthermore, the part of the device designed to illuminate the head allows movement of the head to a person being treated. In this manner, the treatment may be more effective and the time required for a single treatment may be minimized.

According to another aspect, a method of performing light therapy on a subject is provided. The method comprises the provision of a lighting system as previously described. The method further involves the positioning the head set on the person's head, positioning the beam fitting over the person's trunk and loin, substantially parallel to a long central body axis, and illuminating the portions of the person's body corresponding to chakra points by means of the first set of light sources and the second set of light sources, with light emission characteristics of the light sources being controlled by the control unit.

BRIEF DESCRIPTION OF DRAWINGS

Embodiments will now be described, by way of example only, with reference to the accompanying schematic drawings in which corresponding reference symbols indicate corresponding parts, and in which:

FIG. 1 schematically shows a perspective view of an embodiment of the light therapy device.

FIG. 2a shows a side view of the beam fitting comprising the light sources for illuminating specific regions of the individual's trunk. FIG. 2b shows a top view of this beam fitting.

DETAILED DESCRIPTION

Figure 3A:
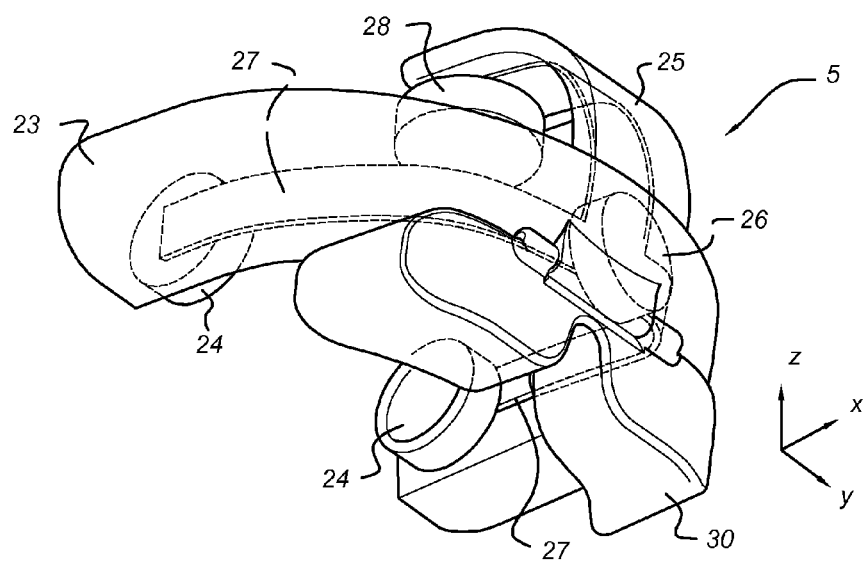
FIGS. 3a and 3b show perspective and bottom views of the head piece comprising the light sources for illuminating specific regions of the head.

The device according to an embodiment of the invention is designed to direct a pre-determined spectrum of light energies and momentum properties to specific areas on an individual's body. In a preferred embodiment, these areas correspond to the so called chakra points.

The exposure of the body to light is accomplished by means of a multi-lamp lighting system that has nine independent light sources. Five of these light sources are fixed to a beam shaped fitting covering the trunk while the four remaining light sources are mounted in a head set. In addition, the beam fitting for illuminating the trunk is mounted to an adjustable stand by means of a pivot, enabling the beam fitting to be spatially adjustable in order to achieve the optimal orientation with respect to the human body.

Illumination characteristics of the individual light sources can be controlled. In addition to selecting specific frequencies and intensity values, a method is provided for controlling the polarization of the individual light sources, enabling for example the exposure to circularly polarized light with corresponding angular momentum characteristics.

Furthermore, the temporal characteristics of the exposure can be controlled, enabling illumination by any desired pulse sequence. Selection of particular frequencies and polarizations is accomplished by combining a proper set of optical elements. The lighting system may hold the light source which projects light through the optical elements 1, focusing a selected portion of the light on a preferred area of the human body.

FIG. 1 schematically shows a perspective view of an embodiment of the light therapy device or lighting system 1. The lighting system comprises a beam fitting 2, a head set 5 and a control unit CU. The beam fitting and head set comprise light sources 12, 14, 16, 18, 20, 24, 26, 28 with predetermined and/or controllable light emission characteristics.

An adjustable support 6 provides a means of suspending the beam fitting in any desirable orientation with respect to an arbitrarily positioned person. The head set 5 further comprises a set of display goggles 30, covering the person's eyes.

The head set 5 is intended to be positioned on the person's head and the beam fitting is intended to be positioned over the trunk and loin, substantially parallel to the long central body axis. It is envisioned that for chakra therapy, the body regions destined for illumination correspond to chakra points.

The head set 5 is designed as a separated unit with respect to the beam fitting 2 and the support 6. Power and control signals for the light sources and the virtual display goggles 30 within the head set are received by means of an electrical connection 22 with the beam fitting. In an alternative embodiment, the head set may be fitted with a local power supply, while receiving control signals for the light sources and virtual display goggles 30 by remote means of communication, e.g. electromagnetic waves.

So, in an embodiment, the lighting system comprises a beam fitting 2, a head set 5, and a control unit CU. The beam fitting 2 extends in a longitudinal direction and comprises a first set of light sources 12, 14, 16, 18, 20. The head set 5 comprises a second set of light sources 24, 26, 28. Each light source of the first set and second set of light sources is connected to the control unit CU. The control unit is arranged for controlling the emission characteristics of each of the light sources, the light sources of the first set being arranged along the longitudinal direction of the beam fitting at first predetermined locations and the light sources of the second set being arranged at second pre-determined locations on the head set.

FIGS. 2a and 2b show a top view and a side view of the beam fitting 2. In an embodiment, the bulk of the beam fitting comprises a first beam segment 3 and a second beam segment 4. The first beam segment 3 is directed at an angle with respect to the second beam segment 4. The angle may be substantially equal to 90, corresponding to substantially perpendicular beam segments.

Furthermore, each light source in the first set of light sources 12, 14, 16, 18, 20 is at a predetermined location. A first light source 12 is arranged in the first beam segment 3. This first beam segment is arranged to be positioned adjacent to a groin region of the human being, with the first light source 12 arranged to illuminate the groin region. Second, third, fourth and fifth light sources 14, 16, 18, 20 of the first set are arranged in the second beam segment 4, the second beam segment arranged for being positioned along a longitudinal direction of a trunk of the human being. The light sources at the first predetermined locations are arranged for illuminating specific portions of the trunk. The predetermined locations may correspond to chakra positions on the trunk of the human body.

Each light source in the beam fitting 2 requires a recess 19 for holding the corresponding light source. A top of the recess 19, the top-side with respect to the beam fitting 2 corresponding to the positive x-direction in the set of axes displayed in FIGS. 2a and 2b, allows for repositioning of the individual light source. A bottom of the recess 19, the bottom-side with respect to the beam fitting 2 corresponding to the negative x-direction, offers an aperture for the emitted light to be directed at a body region. The light sources are attached to the beam fitting 2 in a way that allows for repositioning of each light source substantially along the longitudinal axis of the beam fitting 2. This allows for variation of the mutual distance between the light sources, adapting this distance to the body characteristics of different individuals. The motion is confined by constructional properties like the recesses 19 and the means of attachment of the light sources to the beam fitting.

Figure 3B:
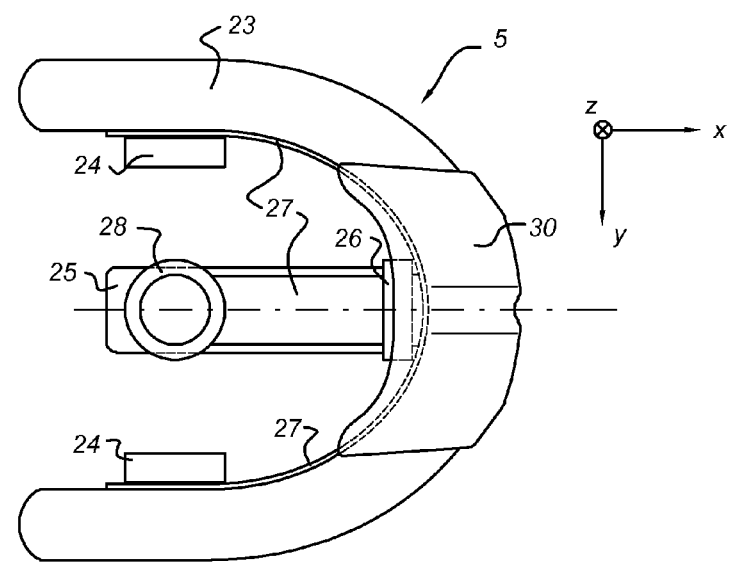

FIGS. 3a and 3b show a perspective view and a bottom view of the head set 5. The head set 5 is designed to be positioned at the upper part of the head of a human being. A first arched support portion 23 is arranged to cover the brow of the head. A second arched support portion 25 is attached at one end to a center location of the first arched support portion 23 in a substantially perpendicular fashion to the first arched support portion. The second arched support portion 25 is arranged for extending from the brow to a crown of the head.

The head set 5 comprises a second set of light sources 24, 26, 28, although the spatial separation between this set and the first set of light sources in the beam fitting 2 should not be considered to imply any functional difference. The light source 26 located at the symmetry axis of the first arched support portion 23 is at a fixed position attached to the first arched support portion. The remaining three light sources 24, 28 are movably mounted to arched rails 27 tangent to the first arched support portion 23 and the second arched support portion 25. The arched rails 27 are arranged to follow the local curvature of the individual's head. The remaining three light sources 24, 28 can therefore be repositioned along substantially concentric trajectories.

In an embodiment of the lighting system, the light sources in the head set 5 are arranged to direct their light energy at the forehead, the temples and the crown of the human being. In the embodiment of the lighting system envisioned for chakra therapy, the light source near the forehead 26 is arranged to generate purple light, and the light sources near the temples 24 and the light source near the crown 28 is arranged to emit white light.

In a further embodiment, the head set 5 comprises a set of virtual display goggles 30. While in use, the virtual display goggles cover the eyes of a human being and are arranged for displaying a sequence of calming images or patterns, thereby making the user feel more at ease and reducing tension induced movements. The virtual display goggles 30 may be connected to the control unit CU, which is arranged for controlling calming patterns displayed by the virtual display goggles. Preferably, the control unit is fitted with a means of storing and executing a program of user specific settings, including a pre-selected set of calming patterns.

Figure 4:
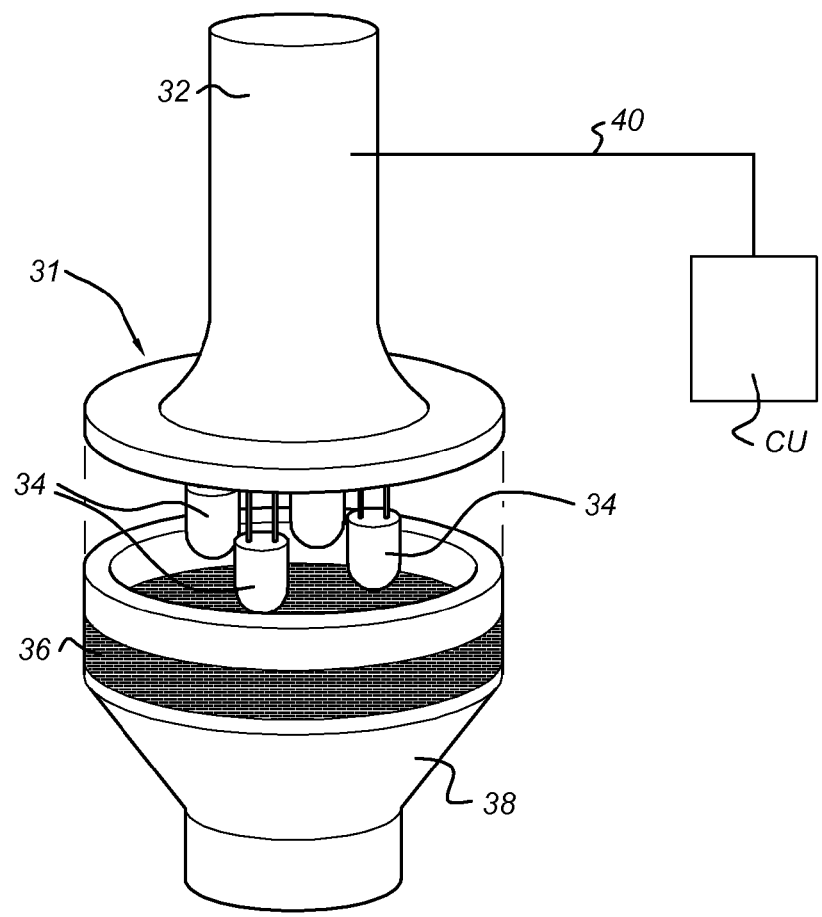
FIG. 4 presents a schematic view of a single light source.

FIG. 4 shows a detailed view of a light source 12, 14, 16, 18, 20, 24, 26, 28. In an embodiment of the lighting system, at least one light source of the first and second set comprises one or more light emitting diodes 34, a filter 36, a transparent object 38 and a housing 31. The light emitting diodes 34, which are arranged in the housing 31, constitute the primary source of light. The emitted light is directed at a filter 36, which function is to transmit a desired set of light frequencies and polarizations while preventing the transmission of light with unwanted characteristics. Construction of the light therapy device allows the filter to be easily removed or substituted by a different filter of choice. The light traversing the filter 36 will subsequently encounter a transparent object 38, the filter being arranged in between the one or more light emitting diodes 34 and the transparent object. This transparent object is arranged at an opening of the housing 31. The first purpose of this transparent object 38 is to act as a lens, directing the emitted light at desired regions on the individual's body. The transparency of this transparent object 38 pertains to the desired light frequencies and polarizations, therefore a second purpose of the transparent object 38 is that it may have additional light filtering properties.

In addition, the transparent object 38 may be a dispersive medium for separating the frequency components of the light emanating from the light source, redirecting each frequency component to a different part of the body. The transparent object 38 may have a crystalline or glass composition, or may consist of another known compound possessing a frequency dependent ability of altering the phase, polarization and/or intensity of the transmitted light.

In chakra therapy, it is held that the amount of rotation in the light beam is a significant contributor to the effectiveness of treatment. In an embodiment, at least one light source is arranged for providing a rotation to radiation emitted by the light source. This may be achieved by incorporating an actuator in a light source. This actuator may be arranged to rotate an element of the light source selected from the group consisting of the light emitting diodes, the filter and the transparent object. In this way, the focal points can be repositioned, and the dispersion effects and/or the polarization properties of the projected light can be altered. In an embodiment, at least one light source in the beam fitting 2 is arranged in a corresponding recess 19 comprising an actuator arranged for providing such a rotation effect to the radiation emitted by the light source. As in optics the angular momentum density of electromagnetic waves also represents a form of rotation, it is envisioned in addition that the filter 36 and the transparent object 38 may be capable of transmitting elliptically polarized light.

Furthermore, in an embodiment one or more light sources in the first set of light sources 12, 14, 16, 18, 20 may be arranged with a handle 32 for enabling the light source to be manually repositioned.

In an embodiment of the light therapy device, one or more of the handles 32 are composed of transparent material, enabling a certain amount of the emitted light to be radiated upward, away from the human body. Therefore, at least one light source in the lighting system is arranged in a corresponding recess 19 in the beam fitting 2, the recess being arranged for adjusting the first pre-determined location of the at least one light source along the longitudinal direction.

In an embodiment of the light therapy device, the light emitting diodes 34 are arranged to generate multiple colors. This may be achieved by RGB-light emitting diodes, which are able to mix proper components of red, green and blue light. Furthermore, a pulse sequence, which is a variation of the light intensity in time, may be varied for each light source. Here, temporal variation of the combined properties of intensity, color and rotation is called illumination mode of a light source. Selection and control of the illumination mode for each light source is accomplished by a control unit CU. In an embodiment, the control unit CU is arranged for controlling the illumination mode of each light source by operating the power supply for each light source and/or the actuator in the recess. The control unit CU may comprise a processor for controlling the illumination modes. Preferably, the processor comprises a means for programming a sequence of illumination modes adapted to the individual's needs. For this, the control unit is fitted with a means of storing and executing a program of user specific settings including a sequence of illumination modes. The control unit is connected to the light sources by a further electrical connection 40.

The descriptions above are intended to be illustrative, not limiting. It will be apparent to the person skilled in the art that alternative and equivalent embodiments of the invention can be conceived and reduced to practice, without departing from the scope of the claims set out below.

LIST OF FIGURE ELEMENTS

1: lighting system
2: beam fitting
3: first beam segment
4: second beam segment
5: head set
6: adjustable support
12: first light source (red, groin)
14: second light source (orange, belly)
16: third light source (yellow, plexus solaris)
18: fourth light source (green, sternum)
19: recess
20: fifth light source (blue, throat)
22: electrical connection
23: first arched support portion
24: first pair of light sources (white, temples)
25: second arched support portion
26: sixth light source (purple, forehead)
27: arched rails
28: seventh light source (white, crown)
30: virtual display goggles
31: housing
32: handle
34: light emitting diode
36: filter
38: transparent object
40: further electrical connection
CU: control unit

The invention claimed is:

1. A lighting system, comprising:
an adjustable stand;
an elongated beam fitting extending in a longitudinal direction and mounted to the adjustable stand by a pivot to enable the elongated beam fitting to be spatially adjustable and configured to be positioned over a trunk and a loin of a human being substantially parallel to a long central body axis, the elongated beam fitting comprising
a first set of light sources disposed along the longitudinal direction of the beam fitting at first predetermined locations, at least one light source of the first set being configured to illuminate trunk and loin portions of the human being when the beam fitting is positioned over the trunk and loin, the at least one light source of the first set being provided in a recess in the beam fitting, the recess being configured to adjust the first predetermined location of the at least one light source within the recess along the longitudinal direction,
a first beam segment, and
a second beam segment, the first beam segment being directed at an angle with respect to the second beam segment;
a head set separated with respect to the beam fitting and configured to be positioned on a head of the human being, the head set comprising a second set of light sources disposed at second predetermined locations on the head set and configured to direct light energy at a forehead, temples and a crown of the human being; and a control unit, each light source of the first set and second set of light sources being connected to the control unit, the control unit being configured to control emission characteristics of each of the light sources.

2. The lighting system according to claim 1, wherein the head set comprises a first arched support portion and a second arched support portion, the second arched support portion being connected at one end to a center location of the first arched support portion, the first arched support portion being configured to cover a brow of a human being, the second arched support portion being configured to extend from the brow to the crown of the human being.

3. The lighting system according to claim 1, wherein the angle is substantially perpendicular.

4. The lighting system according to claim 1, wherein a first light source of the first set is arranged in the first beam segment, the first beam segment configured to be positioned adjacent to a groin region of the human being, the light source being configured to illuminate the groin region.

5. The lighting system according to claim 1, wherein second, third, fourth and fifth light sources of the first set are arranged in the second beam segment, the second beam segment configured to be positioned along a longitudinal direction of the trunk of the human being, the light sources provided at the first predetermined locations being arranged for illuminating portions of the trunk.

6. The lighting system according to claim 1, wherein the head set comprises virtual display goggles configured to cover eyes of the human being and being connected to the control unit, the control unit being configured to control images to be displayed on the virtual display goggles.

7. The lighting system according to claim 1, wherein the at least one light source of the first and second set comprises one or more light emitting diodes, a filter, a transparent object and a housing, the one or more light emitting diodes being arranged in the housing as a source of light, the transparent object being arranged at an opening of the housing and configured to output light emitted by the one or more diodes, the filter being arranged between the one or more light emitting diodes and the transparent object.

8. The lighting system according to claim 7, wherein the filter and the transparent object are configured to transmit elliptically polarized light.

9. The lighting system according to claim 7, wherein the at least one light source is provided with an actuator that is configured to rotate an element selected from the group consisting of the light emitting diodes, the filter and the transparent object.

10. The lighting system according to claim 9, wherein the control unit is configured to control the actuator in the recess.

11. The lighting system according to claim 1, wherein the control unit is configured to control the intensity of at least one of the light sources as a function of time.

12. A method of performing light therapy on a human being, comprising:

providing a lighting system comprising
an adjustable stand,
an elongated beam fitting extending in a longitudinal direction and mounted to the adjustable stand by a pivot and configured to be positioned over a trunk and a loin of a human being substantially parallel to a long central body axis, the elongated beam fitting comprising
a first set of light sources disposed along the longitudinal direction of the beam fitting at first predetermined locations, at least one light source of the first set being configured to illuminate trunk and loin portions of the human being when the beam fitting is positioned over the trunk and loin, the at least one light source of the first set being provided in a recess in the beam fitting, the recess being configured to adjust the first predetermined location of the at least one light source within the recess along the longitudinal direction,
a first beam segment, and
a second beam segment, the first beam segment being directed at an angle with respect to the second beam segment,
a head set separated with respect to the beam fitting and configured to be positioned on a head of the human being, the head set comprising a second set of light sources disposed at second predetermined locations on the head set and configured to direct light energy at a forehead, temples and a crown of the human being, and
a control unit, each light source of the first set and second set of light sources being connected to the control unit, the control unit being configured to control emission characteristics of each of the light sources;
positioning the head set on the head;
positioning and spatially adjusting the beam fitting over the trunk and the loin substantially parallel to the long central body axis;
illuminating portions of the body of the human being corresponding to chakra points by the first set of light sources and the second set of light sources, the emission characteristics of the light sources being controlled by the control unit.

* * * * *